(12) United States Patent
De Lucchi et al.

(10) Patent No.: US 9,481,680 B2
(45) Date of Patent: Nov. 1, 2016

(54) PROCESS FOR THE PREPARATION OF KEY INTERMEDIATES OF OMARIGLIPTIN

(71) Applicant: F.I.S.—FABBRICA ITALIANA SINTETICI S.P.A., Montecchio Maggiore (VI) (IT)

(72) Inventors: Ottorino De Lucchi, Venice (IT); Enrico Rosso, Venice (IT); Simone Zaramella, Vigodarzere (IT); Stefano Tartaggia, Venice (IT)

(73) Assignee: F.I.S.—FABBRICA ITALIANA SINTETICI S.P.A, Montecchio Maggiore (VI) (IT)

(*) Notice: Subject to any disclaimer, the term of this patent is extended or adjusted under 35 U.S.C. 154(b) by 0 days.

(21) Appl. No.: 14/900,858

(22) PCT Filed: Jan. 19, 2015

(86) PCT No.: PCT/EP2015/050858
§ 371 (c)(1),
(2) Date: Dec. 22, 2015

(87) PCT Pub. No.: WO2015/139859
PCT Pub. Date: Sep. 24, 2015

(65) Prior Publication Data
US 2016/0200727 A1 Jul. 14, 2016

(30) Foreign Application Priority Data
Mar. 20, 2014 (IT) ................ VI2014A0064

(51) Int. Cl.
*C07C 271/18* (2006.01)
(Continued)

(52) U.S. Cl.
CPC ........... *C07D 487/04* (2013.01); *C07C 221/00* (2013.01); *C07C 225/10* (2013.01); *C07C 225/16* (2013.01); *C07C 245/24* (2013.01); *C07C 269/08* (2013.01); *C07D 309/14* (2013.01)

(58) Field of Classification Search
CPC . C07C 271/18; C07C 221/00; C07C 225/10; C07C 245/24; C07D 309/14; C07D 487/04
See application file for complete search history.

(56) References Cited

U.S. PATENT DOCUMENTS

2009/0187028 A1* 7/2009 Xu ................. C07C 269/06
548/218

FOREIGN PATENT DOCUMENTS

| WO | 2010056708 A1 | 5/2010 |
| WO | 2013003249 A1 | 1/2013 |
| WO | 2013003250 A1 | 1/2013 |

OTHER PUBLICATIONS

CAS Registry—Otava Chemicals (Mar. 2011).*
(Continued)

*Primary Examiner* — Valerie Rodriguez-Garcia
(74) *Attorney, Agent, or Firm* — Lucas & Mercanti, LLP

(57) ABSTRACT

An improved process for the preparation of a key intermediate for the synthesis of the active ingredient Omarigliptin is provided. The key intermediate is a compound having the following formula (I)

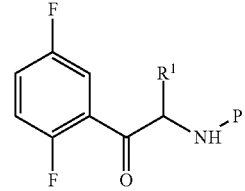

(I)

wherein $R^1$ is propargyl or allyl group and P is an amine protecting group. The compound of formula (I) is prepared by converting a compound of formula (IV)

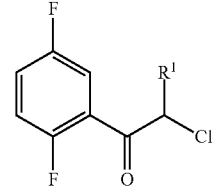

(IV)

by an amination reaction to a compound of formula (III),

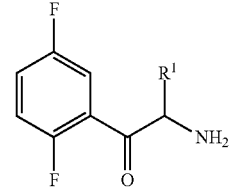

(III)

which is then protected to provide a compound of formula (II),

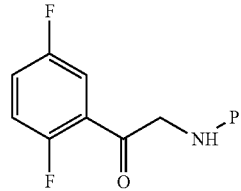

(II)

which is then alkylated to provide the compound of formula (I).

17 Claims, No Drawings

(51) Int. Cl.
*C07C 221/00* (2006.01)
*C07C 225/10* (2006.01)
*C07C 245/24* (2006.01)
*C07D 309/14* (2006.01)
*C07D 487/04* (2006.01)
*C07C 225/16* (2006.01)
*C07C 269/08* (2006.01)

(56) References Cited

OTHER PUBLICATIONS

International Search Report for International Application No. PCT/EP2015/050858. (Mar. 9, 2015) (3 pages).
Conrad et al., "A practical one-pot process for alpha-amino aryl ketone synthesis", Tetrahedron Letters, 2005, vol. 46, No. 49, pp. 8587-8589.

* cited by examiner

PROCESS FOR THE PREPARATION OF KEY INTERMEDIATES OF OMARIGLIPTIN

CROSS-REFERENCE TO RELATED APPLICATIONS

This application is a 371 of PCT/EP2015/050858 filed Jan. 19, 2015, which claims the benefit of Italian Patent Application No. VI2014A000064, filed Mar. 20, 2014.

TECHNICAL FIELD

The present invention refers to an improved process for the preparation of key intermediates for the synthesis of the dipeptidyl peptidase-IV inhibitor named Omarigliptin.

BACKGROUND ART

The present invention relates to a convenient process for the preparation of a key intermediate for the synthesis of a dipeptidyl peptidase-IV inhibitor (DP-IV). In particular, the compound named Omarigliptin or (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine, having the following structure:

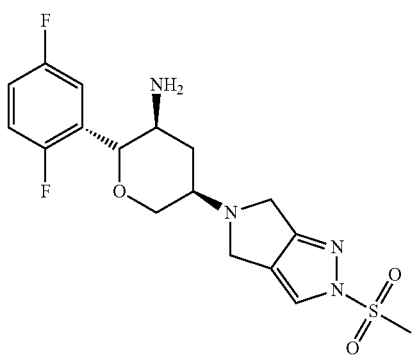

is an active pharmaceutical ingredient which acts as a potent inhibitor of dipeptidyl peptidase-IV, therefore, useful to treat type 2 diabetes, obesity and high blood pressure.

The patent publication WO2010/056708 in the name of Merck & Co., discloses a class of aminotetrahydropyrans, which are potent inhibitors of DP-IV and therefore useful for the treatment of Type 2 diabetes and, in particular, specifically discloses for the first time the compound said above.

The active compound (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine is prepared in example 1 by coupling of the key intermediate 2 named tert-butyl [(2R,3S)-2-(2,5-difluorophenyl)-5-oxotetrahydro-2H-pyran-3-yl]carbamate and having the following structure:

Intermediate 2

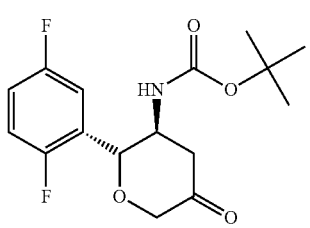

with the Intermediate 5 named 2-(methylsulfonyl)-2,4,5,6-tetrahydropyrrolo[3,4-c]pyrazole and having structure:

Intermediate 5

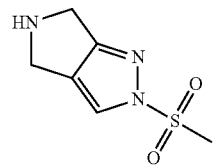

followed by the removal of the Boc protecting group.

The preparation of the Intermediate 2 is also disclosed in details in the same patent publication, as a synthetic method involving nine steps of synthesis, starting from 2,5-difluorobenzaldehyde and the final product was purified by column chromatography.

A shorter process for the preparation of the Intermediate 2 is disclosed in US2009/0187028A1 where it is prepared in four steps from the compound named "Ketone 5" or tert-butyl[1-(2,5-difluorophenyl)-1-oxopent-4-yn-2-yl]carbamate and having the following structure:

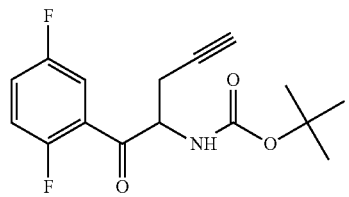 [SMILES: C#CCC(NC(=O)OC(C)(C)C)C(=O)c1cc(F)ccc1F]

Said "Ketone 5" is prepared in four steps starting from ethyl N-(diphenylmethylene)glycinate and introducing the aryl group through a Grignard reaction on the compound 2-bromo-1,4-difluorobenzene.

The same procedure disclosed in Lab scale in US2009/0187028A1 is disclosed in industrial scale in WO2013003249 where the preparation of the Intermediate 2 is again carried out through the preparation of the key intermediate (Ketone 5) of formula:

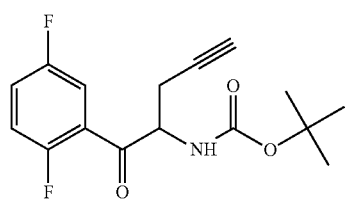 [SMILES: C#CCC(NC(=O)OC(C)(C)C)C(=O)c1cc(F)ccc1F]

The patent publication WO2013003249 also discloses the preparation of the active ingredient (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine using the same synthons as disclosed in WO2010/056708, as said above, but on multi-kilos scale.

It is therefore clear from the prior art that the compound tert-butyl[1-(2,5-difluorophenyl)-1-oxopent-4-yn-2-yl]carbamate and having the following structure:

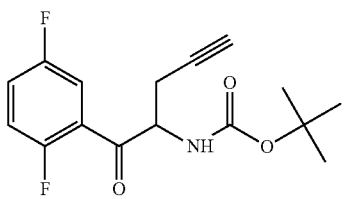 [SMILES: C#CCC(NC(=O)OC(C)(C)C)C(=O)c1cc(F)ccc1F]

as well as derivatives thereof are useful intermediates for the preparation of the active pharmaceutical ingredient named (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine, i.e. Omarigliptin.

Both the methods disclosed in the prior art for the preparation of tert-butyl[1-(2,5-difluorophenyl)-1-oxopent-4-yn-2-yl]carbamate require many synthetic steps, the use of starting materials quite expensive such as 2,5-difluorobenzaldehyde or 2-bromo-1,4-difluorobenzene, the preparation of the Weinreb amide and the use of the Carbonyldiimidazole (CDI).

Moreover, the molar yield of the industrial process disclosed in WO2013003249 for the preparation of the compound tert-butyl[1-(2,5-difluorophenyl)-1-oxopent-4-yn-2-yl]carbamate, when carried out in Lab scale, is around 70% and, the step A, is particularly time consuming, which are both factors not optimal for an industrial production of the active ingredient Omarigliptin.

SUMMARY OF INVENTION

The problem addressed by the present invention is therefore that of providing an improved process for the preparation of tert-butyl[1-(2,5-difluorophenyl)-1-oxopent-4-yn-2-yl]carbamate and analogues thereof which allows to get round to the drawbacks above reported with reference to the known prior art.

This problem is solved by a process for the preparation of a key intermediate for the synthesis of Omarigliptin as outlined in the annexed claims, whose definitions are integral part of the present description.

Further features and advantages of the process according to the invention will result from the description hereafter reported of examples of realization of the invention, provided as an indication and not as a limitation of the invention.

DESCRIPTION OF EMBODIMENTS

Object of the present invention is a process for the preparation of the compound of formula (I):

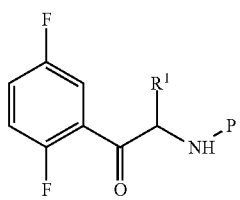
(I)

wherein $R^1$ is propargyl or allyl group and P is a amine protecting group comprising the following steps:
(a) conversion of the compound of formula (IV):

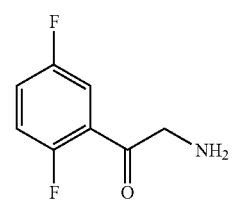
(IV)

to provide the compound of formula (III) or salt thereof:

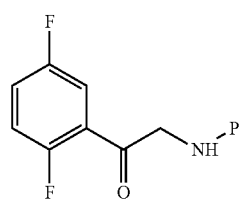
(III)

(b) protection of the compound of formula (III) to provide the compound of formula (II):

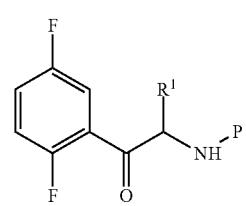
(II)

wherein P is a amine protecting group,
(c) alkylation of the compound of formula (II) to provide the compound of formula (I):

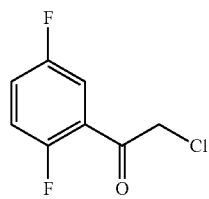
(I)

wherein $R^1$ is propargyl or allyl group and P is an amine protecting group.

P is a amine protecting group which can be selected in the group comprising formyl, acetyl, benzoyl, phenylsulfonyl, tolylsulfonyl, methylsulfonyl, $(CO)OR^2$ or $(CO)R^2$ where $R^2$ is $C_{1-5}$ linear or branched alkyl or $R^2$ is aryl-$C_{0-4}$ alkyl or $C_{0-4}$ alkyl-(unsubstituted or substituted aryl).

The linear or branched $C_{1-5}$ alkyl group of $R^2$ can also be, unsubstituted or substituted with one, two or three substituents chosen in the group of hydroxyl and $C_{1-5}$ alkoxy.

The definition of linear or branched $C_{1-5}$ alkyl thus also includes methyl, ethyl, n-propyl, isopropyl, n-butyl, isobutyl, sec-butyl, tert-butyl, n-pentyl, neopentyl, 1-methylbutyl, 2-methylbutyl, 3-methylbutyl, 1,1-dimethylpropyl, 1,2-dimethylpropyl, 2,2-dimethylpropyl, 1-ethylpropyl.

Preferred P groups are pivaloyl, t-butyloxycabonyl or tert-butyloxycarbonyl (Boc) and benzyloxycabonyl (Z or Cbz).

The substituent $R^1$ is a propargyl, i.e. propyn-2-yl, or is an allyl group.

The compound of formula (III) can be in the form of free base or as a salt.

Preferred salts are those having halides as counter ions, hence, the salt formed with hydrochloric acid or hybrobromic acid (i.e. compound (III) hydrochloride or hydrobromide) are particularly preferred.

It has been indeed surprisingly found that the process of the present invention allows the preparation of the compound of formula (I) in very high molar yield, around 80% which is higher than the molar yield of the know processes.

Moreover, the process according to the present invention involves only three chemical reactions instead of more than six of the known processes, thus simplifying the whole process and drastically reducing the cycle time.

Finally, the process of the present invention avoids the formation of the Weinreb amide and employs as starting material 1,4-diflurobenzene which is less expensive than the more complex compounds 2-bromo-1,4-difluorobenzene and 2,5-difluorobenzaldehyde used in the known processes (see example 1 of US20090187028 or WO2013003249 "INTERMEDIATE I", step B).

All the above factors contribute to make the process of the present invention cheaper, in terms of cost of the compound of formula (I) or of the compound of formula (X), in comparison to the costs of the know processes for the preparation of the compound of formula (I) or (X).

By a chemical point of view, the process of the present invention is quite surprising since the alkylation of the compound of formula (II):

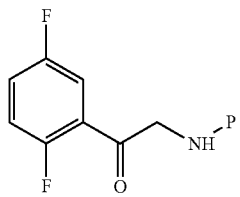

(II)

provides exclusively the compound of formula (I) instead of the compound having the alkyl group on the nitrogen atom. This alkylation step is the key step of the process of the present invention.

According to a preferred embodiment, the step (a) of preparation of the compound (III) is achieved through amination reaction with hexamine (i.e. hexamethylentetramine (HMTA)) since the direct amination with aqueous ammonia in dimethylformamide does not provide the compound of formula (III) but the following by-products:

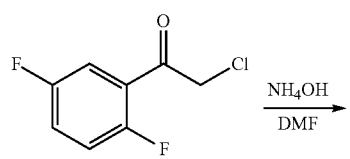

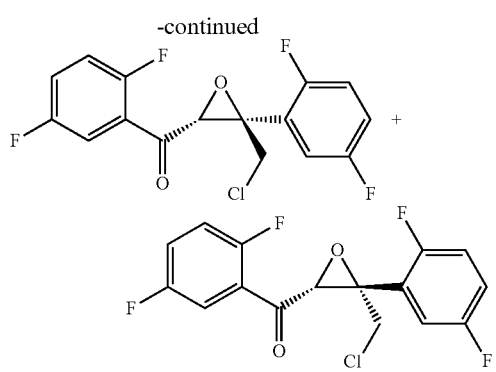

Nevertheless, the amination reaction of the step a) can be carried out also under different conditions (e.g. in absence of water and/or different solvent, temperature, etc.) or with other amination reagents, not only with hexamine, which is the preferred reagent.

Other reagents for amination reaction known to the skilled person can be used to perform the amination reaction of the step (a).

According to an alternative of the process of the present invention, the step (a) is carried out through the following steps:

(a1) conversion of the compound of formula (IV):

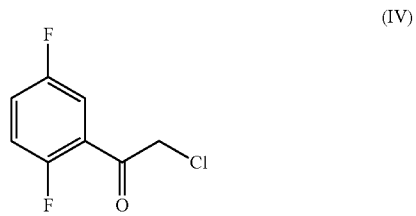 [SMILES: O=C(CCl)c1cc(F)ccc1F]

(IV)

to provide the compound of formula (V):

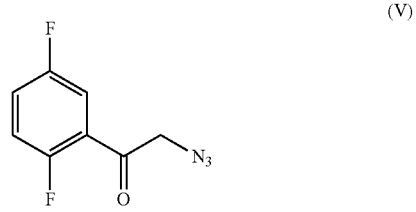 [SMILES: [N-]=[N+]=NCC(=O)c1cc(F)ccc1F]

(V)

(a2) reduction reaction of the compound of formula (V) to provide the compound of formula (III) or salt thereof:

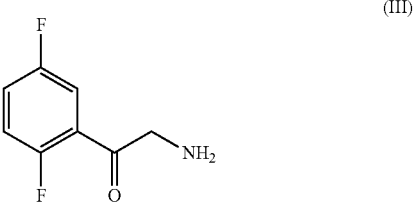 [SMILES: NCC(=O)c1cc(F)ccc1F]

(III)

Other types of amination reactions are also suitable to perform the step (a), e.g. Gabriel or t-BuNH$_2$, etc.

According to a preferred embodiment, the process of the present invention is that where $R^1$ is propyn-2-yl, i.e. propargyl.

According to a preferred embodiment, the process of the present invention is that where P is t-butyloxycarbonyl (Boc).

According to a more preferred embodiment, the process of the present invention is that where $R^1$ is propyn-2-yl, i.e. propargyl and P is t-butyloxycarbonyl (Boc).

The step (c) of the process of the present invention can be carried out by reaction of the compound of formula (II) with an alkylating agent of formula $R^1$—X wherein $R^1$ is propargyl or allyl while X is a leaving group selected in the group comprising halides, aryl solfonates or alkyl solfonates.

Preferred compounds of formula $R^1$—X to perform the step (c) are propargyl bromide or allyl bromide or propargyl benzensolfonate.

The step (c) is carried out in an organic solvent, preferably in DMF.

The step (c) is carried out at temperature comprised between −20° C. and 50° C., preferably between −10° C. and 10° C., preferably is carried out at about 0° C.

The compound of formula (I) wherein $R^1$ is allyl can be converted in the compound named "Intermediate 2" and analogues thereof through the following reaction scheme and using the teaching of US2009/0187028:

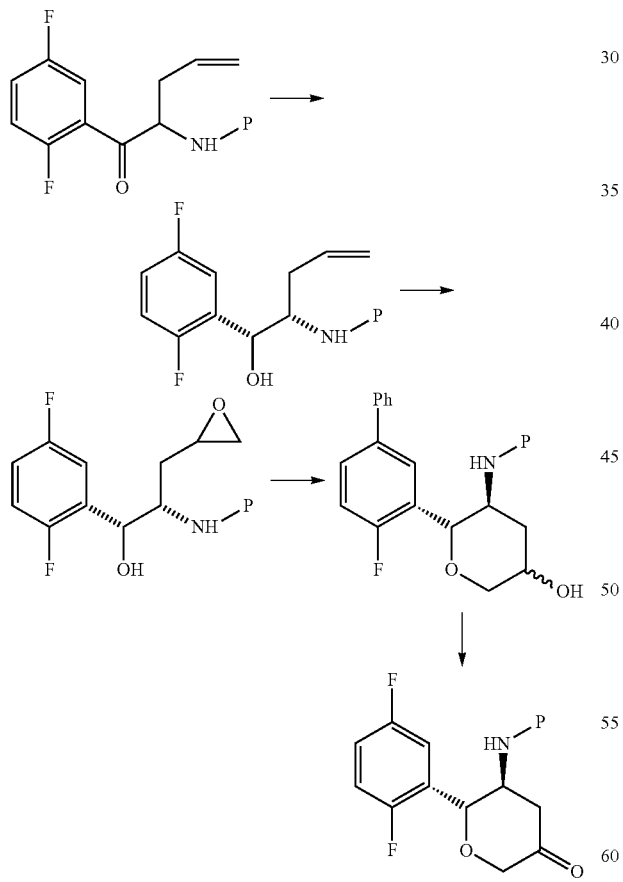

The following compounds are therefore intermediates of the process of the present invention:
the salt of the compound of formula (III) hydrochloride or hydrobromide:

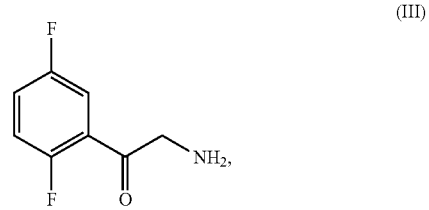 [SMILES: NCC(=O)c1cc(F)ccc1F]

compound of formula (II):

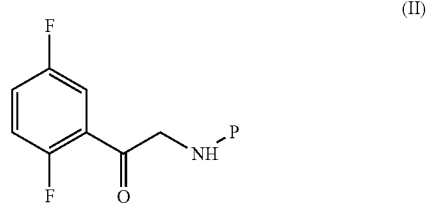

wherein P is an amine protecting group.

According to an embodiment of the present invention, the compound of formula (II) wherein P is t-butyloxycarbonyl or benzyloxycarbonyl is preferred.

The compound of formula (I):

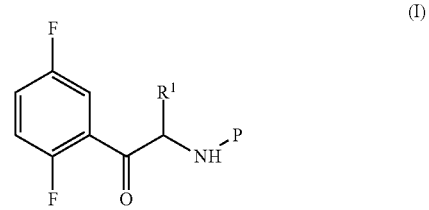

wherein $R^1$ is propargyl or allyl group and P is a amine protecting group, with the exception of the compound where $R^1$ is propyn-2-yl and P is t-butyloxycarbonyl, is a novel intermediate useful for the preparation of the active ingredient Omarigliptin.

According to a preferred embodiment of the invention, compounds of formula (I):

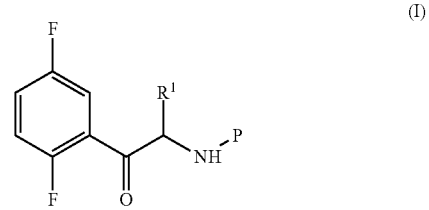

The molar yield of the step (a) of process of the present invention is about 90%, that of step (b) is quantitative and that of step (c) is comprised between 87% and 90%. Therefore the molar yield of the whole process is comprised between 78% and 81%.

which are preferred are those chosen from the group of:
benzyl 1-(2,5-difluorophenyl)-1-oxopent-4-yn-2-ylcarbamate,
benzyl 1-(2,5-difluorophenyl)-1-oxopent-4-en-2-ylcarbamate, tert-butyl 1-(2,5-difluorophenyl)-1-oxopent-4-en-2-ylcarbamate.

Finally, the compound of formula (IV), (III) or salt thereof, or the compound of formula (II) can be thus used for the preparation of the compound of formula (I):

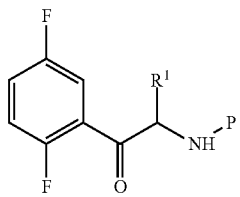
(I)

wherein $R^1$ is propargyl or allyl group and P is an amine protecting group, or for the preparation of the compound of formula (X):

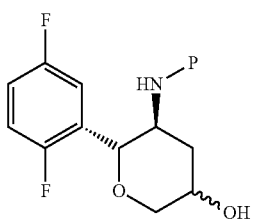
(X)

wherein P is an amine protecting group,
or for the preparation of active ingredient Omarigliptin, as described in the present invention. The compound of formula (I) prepared according to the process of the present invention can be indeed converted into Omarigliptin using the processes known in the prior art.

According to a preferred embodiment of the present invention, the compound of formula (IV), (III) or salt thereof, or the compound of formula (II) are used for the preparation of the preferred compound of formula (I) wherein the substituent $R^1$ is propargyl and P is t-butyloxycarbonyl, or for the preparation of the compound of formula (X) wherein P is t-butyloxycarbonyl.

The compound of formula (I):

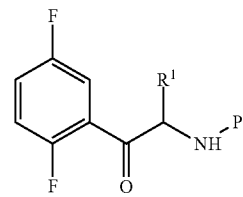
(I)

wherein $R^1$ is propargyl or allyl group and P is a amine protecting group, with the exception of the compound where $R^1$ is propyn-2-yl and P is t-butyloxycarbonyl, can be used for the preparation of the compound of formula (X):

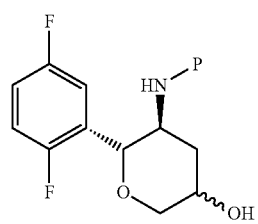
(X)

wherein P is an amine protecting group,
or for the preparation of the active ingredient Omarigliptin.

According to a preferred embodiment the compounds chosen from the group of:
benzyl 1-(2,5-difluorophenyl)-1-oxopent-4-yn-2-ylcarbamate,
benzyl 1-(2,5-difluorophenyl)-1-oxopent-4-en-2-ylcarbamate,
tert-butyl 1-(2,5-difluorophenyl)-1-oxopent-4-en-2-ylcarbamate.

can be suitably used for preparation of the to the compound of formula (X) or for the preparation of the active ingredient Omarigliptin.

The scheme below summarizes the process of the invention for the preparation of the compound of formula (I), including the alternative process to carry out the step (a) through the steps (a1) and (a2).

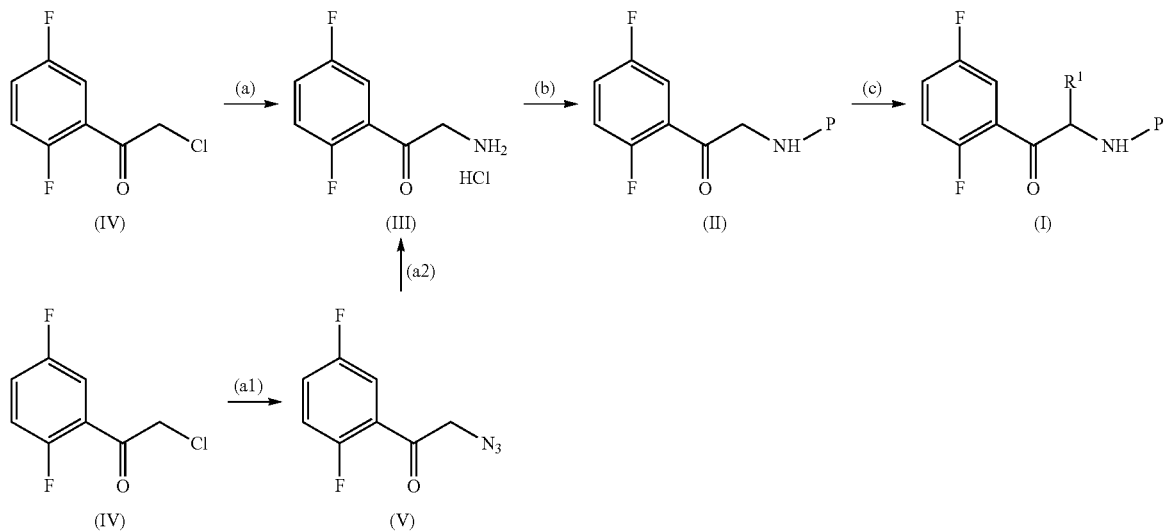

The scheme below shows a preferred embodiment of the invention, i.e. the preparation of the compound of formula (I) wherein R1 is propargyl and P is t-butyloxycarbonyl:

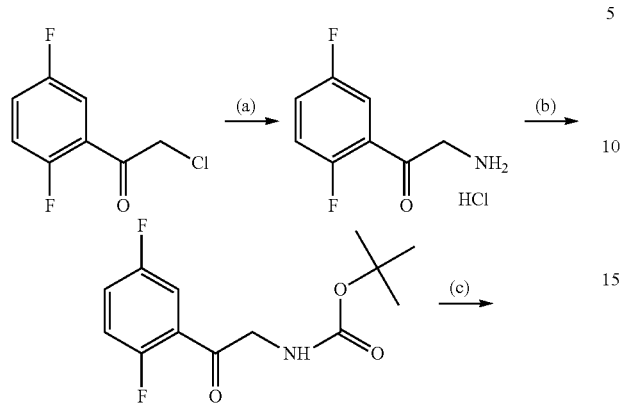

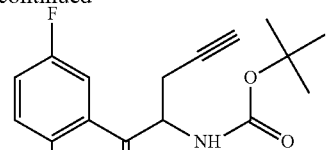

The scheme below shows the conversion of the compound of formula (I), wherein R1 is respectively in the first line propargyl and in the second line is allyl, to the key compound of formula (X) and then, to the active ingredient Omarigliptin of formula (XIV).

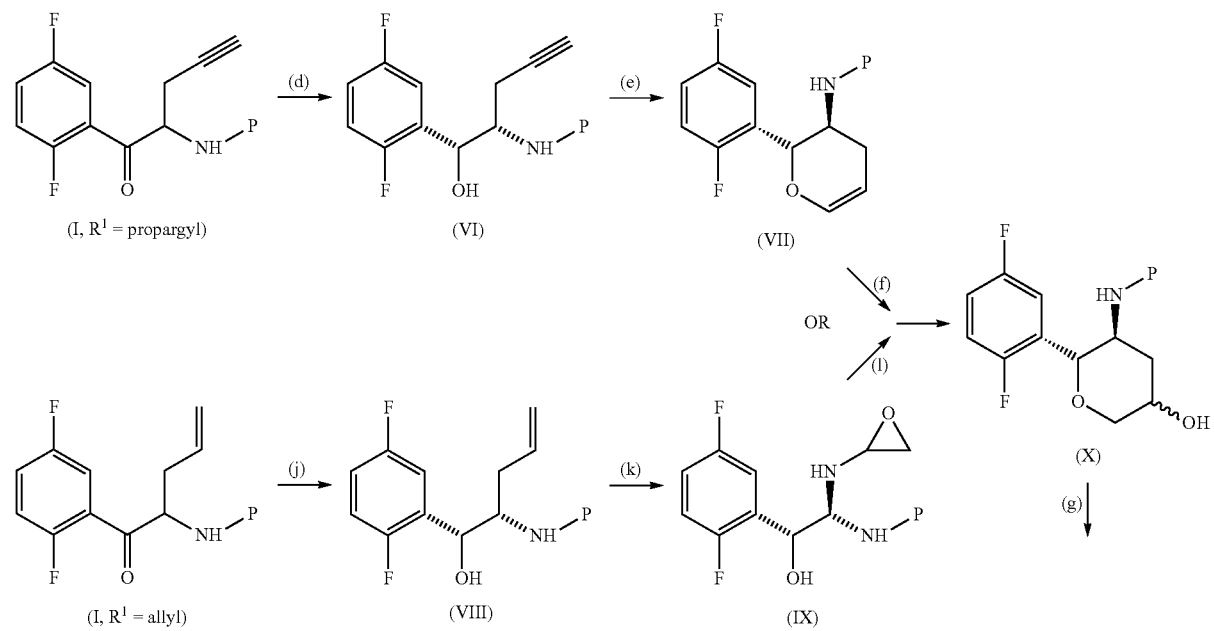

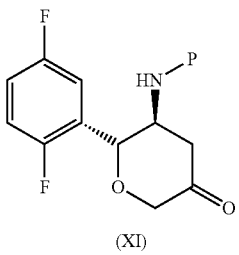

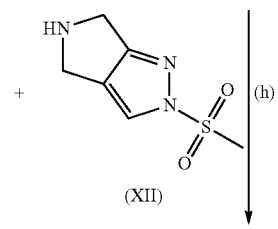

-continued
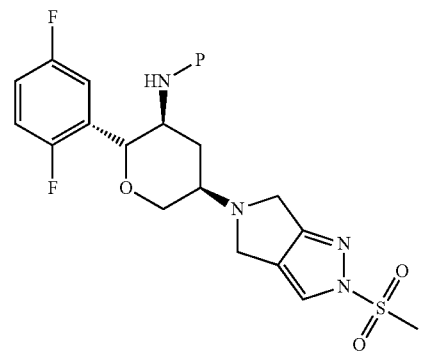
(XIII)
(i) ↓
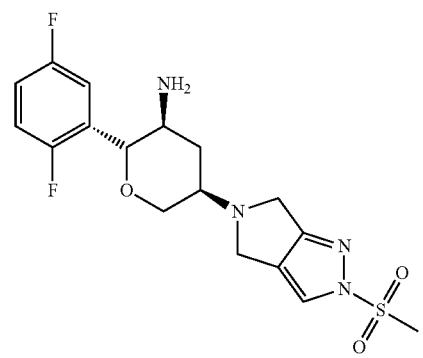
(XIV)
The scheme below shows a preferred embodiment of the invention, i.e. the preparation of the compound of formula (X) and the preparation of Omarigliptin starting from the compound of formula (I) wherein R1 is propargyl and P is t-butyloxycarbonyl:
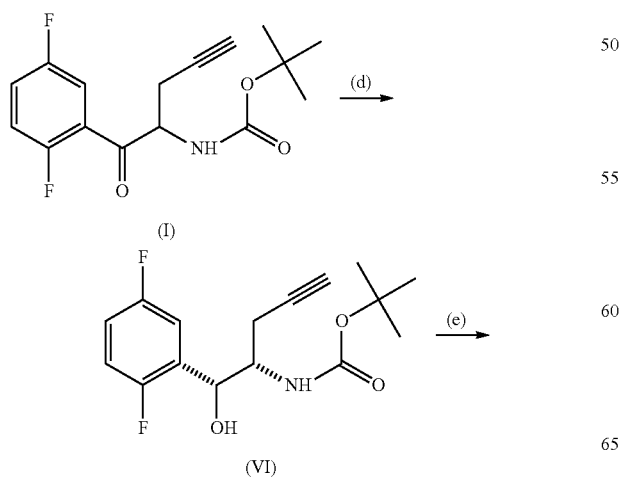
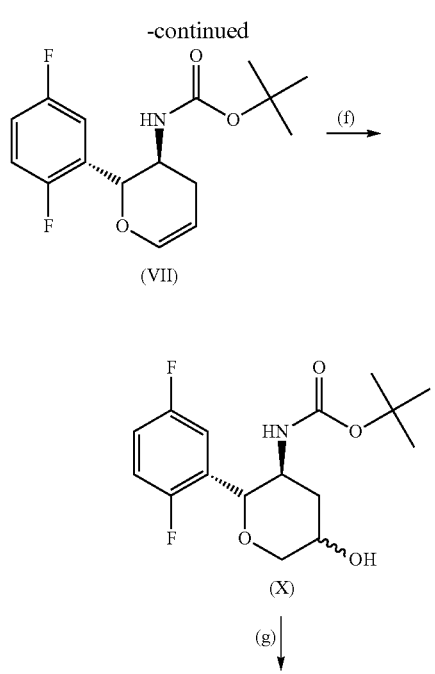

15
-continued

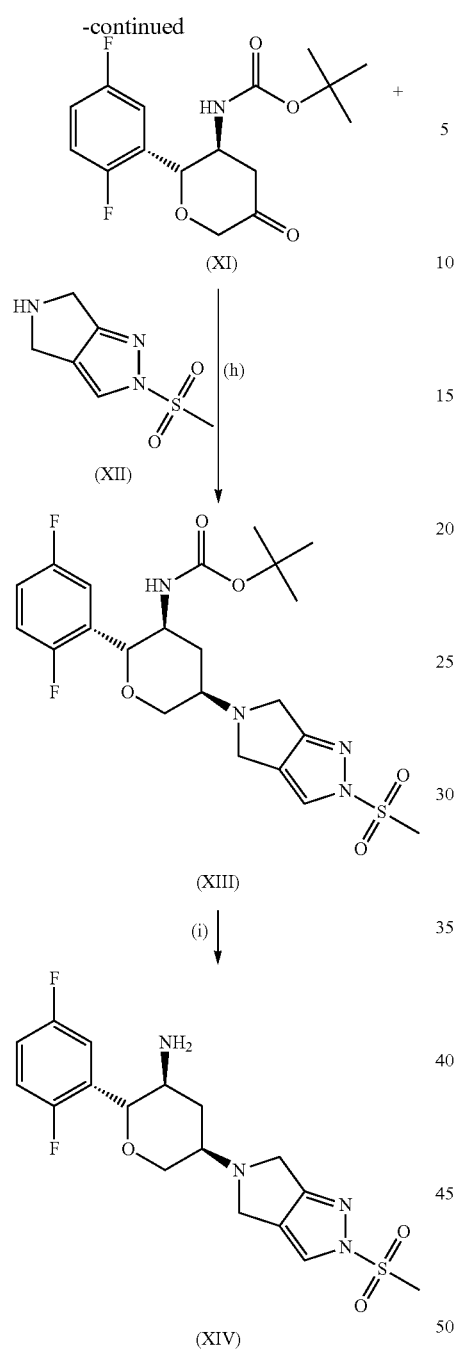

(XI)

(XII)

(h)

(XIII)

(i)

(XIV)

Another aspect of the invention is the process for the preparation of the compound of formula (X):

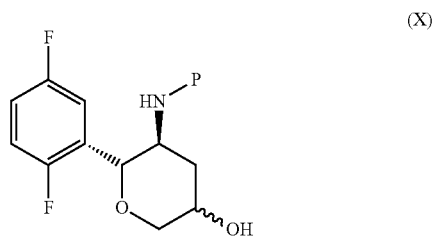

(X)

wherein P is an amine protecting group, comprising the following steps:

A. preparation of the compound of formula (I):

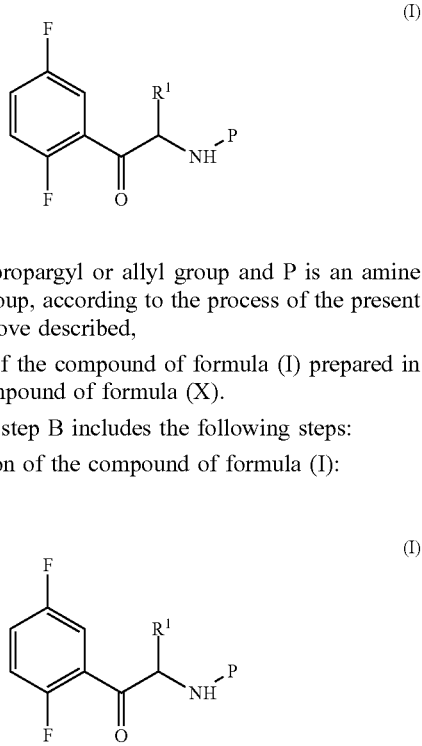

(I)

wherein $R^1$ is propargyl or allyl group and P is an amine protecting group, according to the process of the present invention, above described, B. conversion of the compound of formula (I) prepared in step A to compound of formula (X).

In detail, the step B includes the following steps:

(d) Conversion of the compound of formula (I):

(I)

wherein $R^1$ is propargyl group and P is an amine protecting group, to the compound of formula (VI):

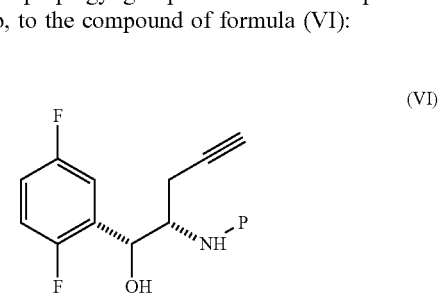

(VI)

wherein P is an amine protecting group;

(e) Conversion of the compound of formula (VI):

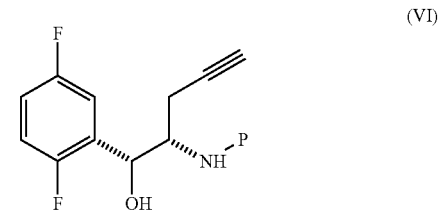

(VI)

wherein P is an amine protecting group, to the compound of formula (VII):

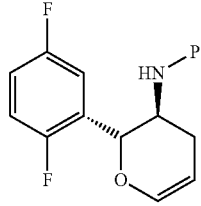

(VII)

wherein P is an amine protecting group, (f) Conversion of the compound of formula (VII):

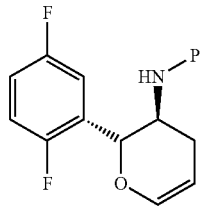

(VII)

wherein P is an amine protecting group,
to the compound of formula (X):

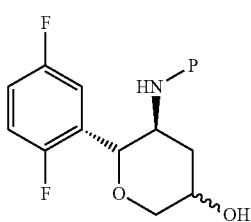

(X)

wherein P is an amine protecting group, or, alternatively, process wherein the steps (d), (e), (f) are substituted by the following steps (j), (k), (l):

(j) Conversion of the compound of formula (I):

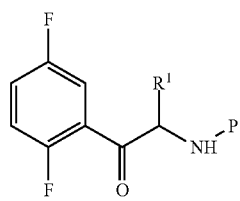

(I)

wherein $R^1$ is allyl group and P is an amine protecting group, to the compound of formula (VIII):

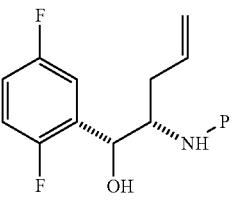

(VIII)

wherein P is an amine protecting group;
(k) Conversion of the compound of formula (VIII):

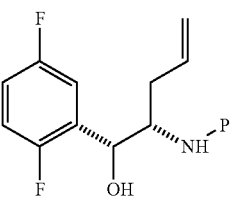

(VIII)

wherein P is an amine protecting group,
to the compound of formula (IX):

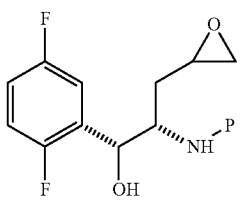

(IX)

wherein P is an amine protecting group,
(l) Conversion of the compound of formula (IX):

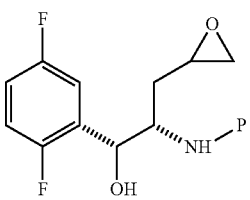

(IX)

wherein P is an amine protecting group,
to the compound of formula (X):

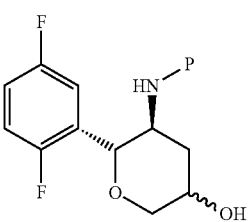

(X)

wherein P is an amine protecting group.

The compound of formula (X):

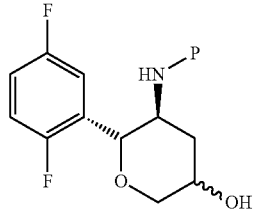

(X)

wherein P is an amine protecting group, prepared according to the process above described can be converted to the active ingredient Omarigliptin of formula (XIV):

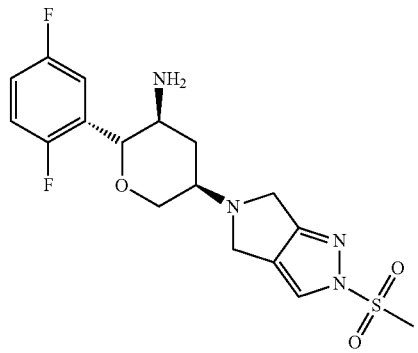

(XIV)

by a process comprising the following further steps:

(g) Conversion of the compound of formula (X):

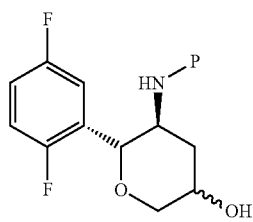

(X)

wherein P is an amine protecting group, to the compound of formula (XI):

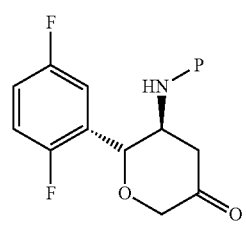

(XI)

wherein P is an amine protecting group, (h) Reaction of the compound of formula (XI):

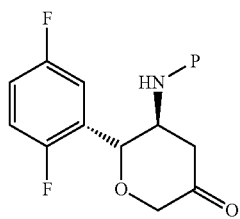

(XI)

wherein P is an amine protecting group, with the compound of formula (XII) or salt thereof:

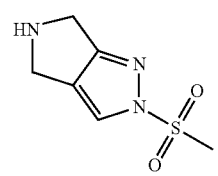

(XII)

to provide the compound of formula (XIII):

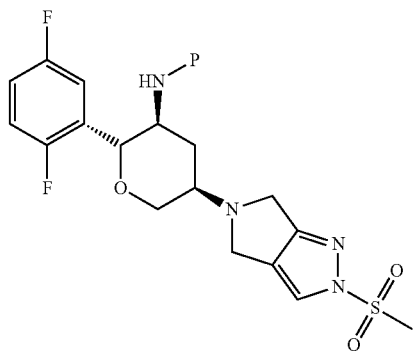

(XIII)

wherein P is an amine protecting group, (i) Conversion of the compound of formula (XIII):

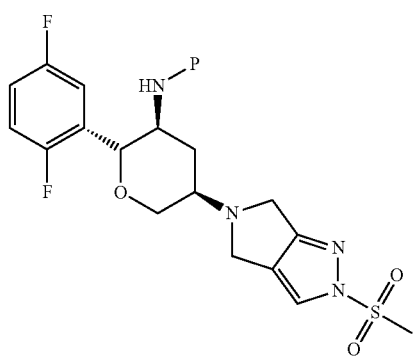

(XIII)

wherein P is an amine protecting group, to Omarigliptin of formula (XIV):

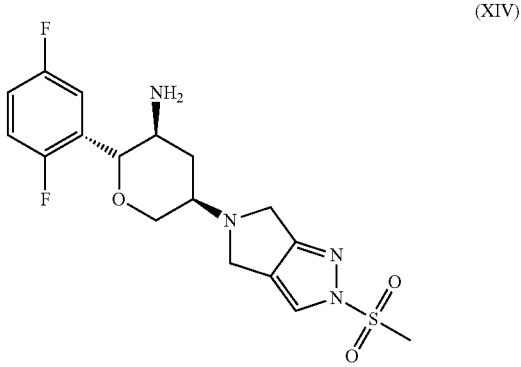

The step (d) can be carried out according to the teaching of WO2013/003249, example "INTERMEDIATE 1", Step C-F, i.e. using 1,4-diazabicyclo[2.2.2]octane and the chiral ruthenium complex catalyst, or according to the teaching of US2009/0187028, step 3.

The step (e) can be carried out according to the teaching of WO2013/003249, example "INTERMEDIATE 1", Step G-J, i.e. using a Ruthenium catalyst or according to the teaching of US2009/0187028, step 4 or alternative step 4.

The step (f) can be carried out according to the teaching of WO2013/003249, example "INTERMEDIATE 1", Step K-N, i.e. using $NaBO_3$ or according to the teaching of US20091/187028, step 5, using $BH_3$—$SMe_2$, thus preparing the compound of formula (X).

According to the alternative route of synthesis for the preparation of the compound of formula (X), using compound (I) wherein R1 is allyl, the step (j) can be carried out under the same conditions above disclosed to carry out the step (d). Alternatively, the conversion of the step (d) can be carried out by hydrogenation with a catalyst enantioselective (e.g. Ru(BINAP)) or using a chiral borane or a ketoreductase enzyme.

The step (k) can be carried out using the typical known reagents to convert a double bond to an epoxide, thus, step (k) can be carried out using for example meta-chloroperbenzoic acid or OXONE or dimethyldioxyirane.

The step (l) according can be carried out teachings of the skilled person regarding the 6-endo-type cyclization of epoxides which also includes ruthenium catalyzed cyclizations as disclosed in J. Am. Chem. Soc., 2004, 126(22), 6895-9, cyclizations performed in water as disclosed in Chem. Soc. Rev., 2009, 38, 3175-3192, and biocatalytic transformations using, for example, Epoxide Hydrolase Lsd19 as disclosed by Y. Shichijo et al., J. Am. Chem. Soc., 130, 12230-12231 (2008), or cyclization in acid medium (e.g. by HCl, $H_2SO_4$, $BF_3$, TFA), or cyclization in basic medium (e.g. with $NEt_3$, $K_2CO_3$).

The preparation of Omarigliptin, stating from the compound of formula (X) prepared according to the process of the inventions, can be carried out using the teachings of WO2013003249, US20090187028 and WO2013003250.

In particular, the step (g) can be carried out according to the teaching of WO2013/003249, example "INTERMEDIATE 1", Step O, or according to the teaching of US2009/0187028, step 6, i.e. using $NaBO_3$ and $RuCl_3$.

The compound of formula (XII) and salts thereof, also as benzensulphonate salt, can be prepared according to the teaching WO2013/003249, "INTERMEDIATE 2", steps from A to F or according to WO2013003250, examples 1-3 or example 6.

The step (h) and (i) can be carried out according to the teaching of WO2013/003249 pag. 15-16, step A and step B and WO2013003250 Example 7, step I and step II or Example 9 step C and step D.

The step (i) of amine deprotection of Omarigliptin, depending on the nature of the protecting group P, can be carried out differently, using the common general knowledge of the skilled person regarding the removal of amine protecting group, evidence of the which can be found in the book of Theodora W Greene with title "Protective Groups in Organic Synthesis" or in the book of Anthony J. Pearson with title "Handbook of Reagents for Organic Synthesis—Activating Agents and Protecting Groups".

According to a preferred embodiment of the process of the present invention, the process for the preparation of the compound of formula (X) and/or the process for the preparation of the active ingredient Omarigliptin are carried out employing compounds of formula (I), (VI), (VII), (VIII), (IX), (X), (XI), (XIII) wherein the amine protecting group P is t-butyloxycarbonyl.

By the description of the invention given above, the process of the present invention allows the preparation of the active ingredient Omarigliptin shortening the synthesis, i.e. shortening the cycling time, increasing the molar yields and using much cheaper raw materials, thus reducing the cost for the whole manufacture of the final product Omarigliptin or intermediates thereof.

EXPERIMENTAL SECTION

Example 1

Synthesis of the Compound of Formula (I) in which P is Boc and $R^1$ is Propargyl According to the Following Scheme

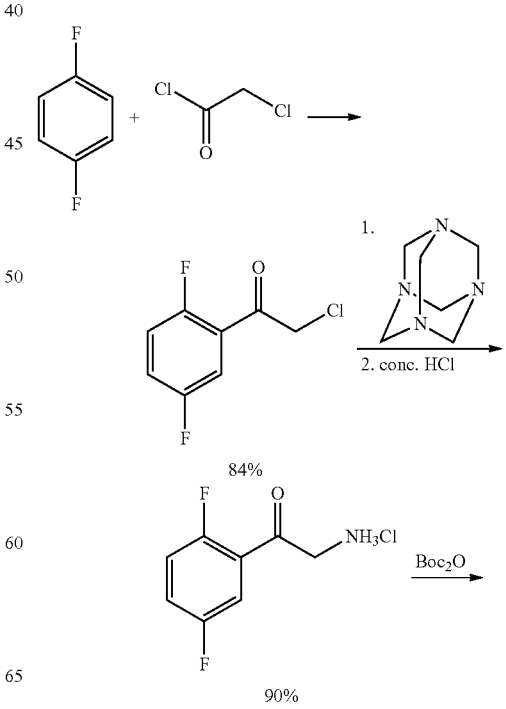

-continued

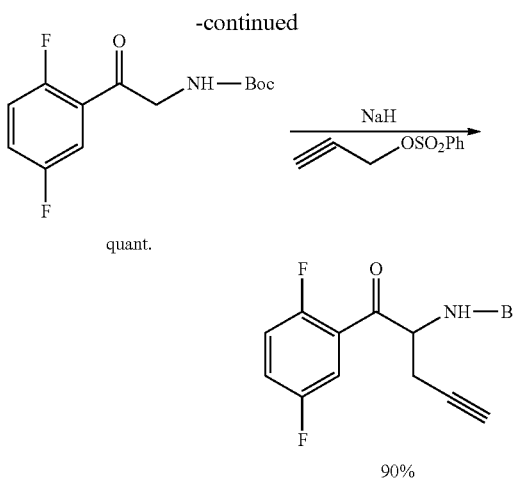

quant.

90%

Synthesis of the Starting Material
2-chloro-1-(2,5-difluorophenyl)ethanone

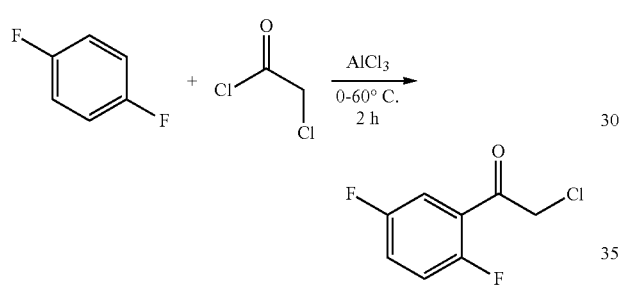

To a suspension of AlCl₃ (34.59 g, 259 mmol) in 1,4-difluorobenzene (20 g, 18.18 mL, 175.3 mmol) at 0° C., chloroacetyl chloride (21.778 g, 192.83 mmol) is added dropwise within 20 min. under stirring. After 1 h at 0° C., the reaction mixture is heated at 60° C. for an extra hour during which time a clear solution is formed. The solution is poured into ca. 400 mL of ice cooled 1M HCl. The colourless solid which precipitates and the solution is extracted with Et₂O (3×50 mL) and the organic phase washed with saturated NaHCO₃ (40 mL), dried (MgSO₄) and concentrated at the rotoevaporator to furnish 27.93 g (84% yield) of colourless crystals.

STEP (a)-Part I: Synthesis of 1-(2,5-difluorophenyl)ethanone-2-hexamethylentetrammonium chloride

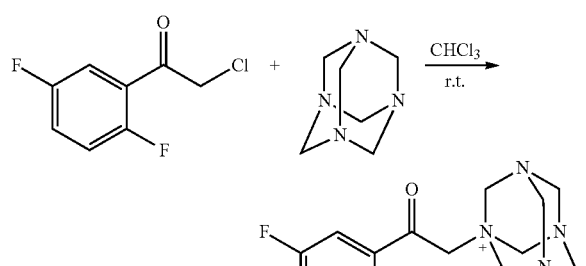

To a solution of 2-chloro-1-(2,5-difluorophenyl)ethanone (1 g, 5.247 mmol) in CHCl₃ (12 mL), Hexamine (also named Hexamethylenetetramine or HMTA) (736 mg, 5.247 mmol) is added while stirring. After refluxing overnight, a colourless solid is formed which is filtered and dried under vacuum to yield virtually quantitative yields of product.

STEP (a)-Part II: Synthesis of 2-(2,5-difluorophenyl)-2-oxoethanammonium chloride

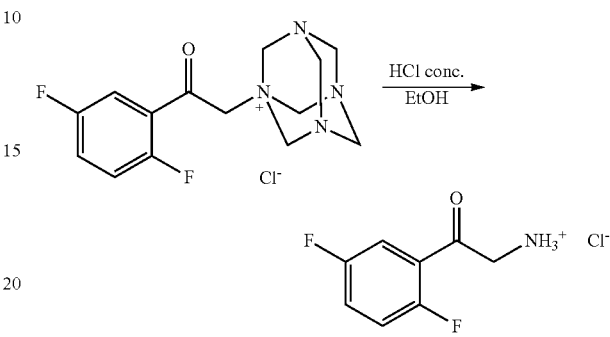

A solution of ethanol (3.2 mL), conc. HCl (0.4 mL) and 1-(2,5-difluorophenyl)ethanone-2-hexamethylentetrammonium chloride (450 mg, 1.36 mmol) is heated at reflux overnight. The reaction mixture is cooled to room temperature, filtered and the mother liquors evaporated to dryness. The solid residue is triturated with water and the aqueous solution evaporated to dryness to obtain 260 mg of 2-(2,5-difluorophenyl)-2-oxoethanammonium chloride (92% yield).

STEP (b): Synthesis of tert-butyl 2-(2,5-difluorophenyl)-2-oxoethyl carbamate

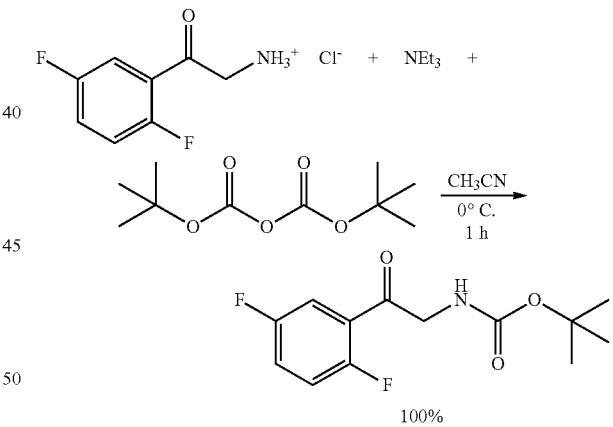

100%

To an ice cooled suspension of 2-(2,5-difluorophenyl)-2-oxoethanammonium chloride (8.937 g, 43.15 mmol) in CH₃CN (90 mL), triethylamine (4.336 g, 6.01 mL, 43.15 mmol) is added dropwise. After stirring at 0° C. for 20 min. Boc₂O (9.417 g, 43.15 mmol) is added. After 40 min. at 0° C., the acetonitrile is removed at the rotoevaporator. Water (200 mL) is added and extracted with Et₂O (3×50 mL). The combined organic phases are washed with brine (3×100 mL) and concentrated at the rotoevaporator to leave 11.7 g of t-butyl 2-(2,5-difluorophenyl)-2-oxoethylcarbamate as a slightly yellow solid (quantitative yields).

$^1$H-NMR (200 MHz, CDCl₃): δ=7.60-7.69 (m, 1 H), 7.09-7.32 (m, 2 H), 5.44 (s, br, 1 H), 4.58 (t, J=4.0 Hz, 2 H), 1.46 (s, 9 H) ppm.

STEP (c): Synthesis of tert-butyl 1-(2,5-difluorophenyl)-1-oxopent-4-yn-2-ylcarbamate Using Propargyl Benzenesulfonate

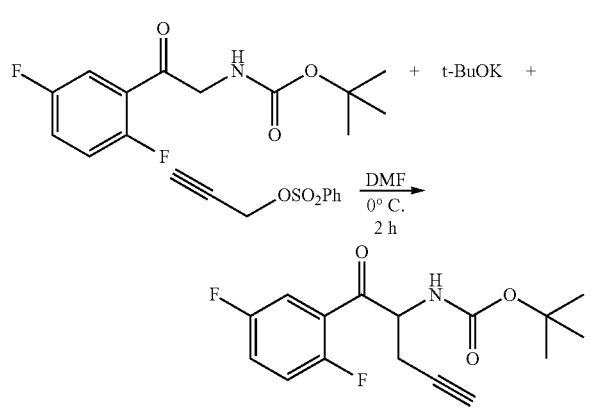

To an ice cooled solution of t-butyl 2-(2,5-difluorophenyl)-2-oxoethylcarbamate (381 mg, 1,404 mmol) in anhydrous DMF (5.8 mL), NaH (60% in mineral oil, 68 mg, 1,685 mmol) is added under Ar. After 20 min. at 0° C., propargyl benzenesolfonate (276 mg, 222 microL, 1,404 mmol) is added to the resulting red coloured solution. The reaction mixture is left reaching room temperature within 2 h. Water (100 mL) is added and extracted with Et$_2$O (3×20 mL). The combined organic phases are washed with brine (3×20 mL), dried (MgSO$_4$) and evaporated at the rotoevaporator to give 380 mg (87% yield) of tert-butyl 1-(2,5-difluorophenyl)-1-oxopent-4-yn-2-ylcarbamate.

Example 2

Synthesis of the Compound of Formula (III) Through the Azide Intermediate of Formula (V)

STEP (a1): Synthesis of 2-azido-1-(2,5-difluorophenyl)ethanone

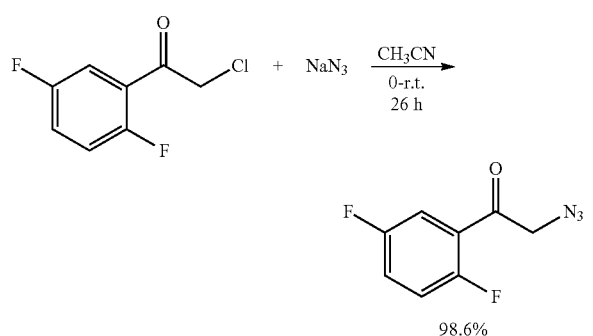

To an ice cooled solution of 2-chloro-1-(2,5-difluorophenyl)ethanone (13.13 g, 68.89 mmol) in acetonitrile (217 mL), sodium azide NaN$_3$ (13.44 g, 206.7 mmol) is added while stirring. The reaction mixture is left reaching rt and kept stirring 26 h. The solid is filtered and the filter washed with ether (2×30 mL). The resulting solution is concentrated to dryness (rotoevaporator) to obtain 13.39 g (99% yield) of a red solid which was directly submitted to hydrogenation without further purification.

STEP (a2): Synthesis of 2-(2,5-difluorophenyl)-2-oxoethanammonium chloride

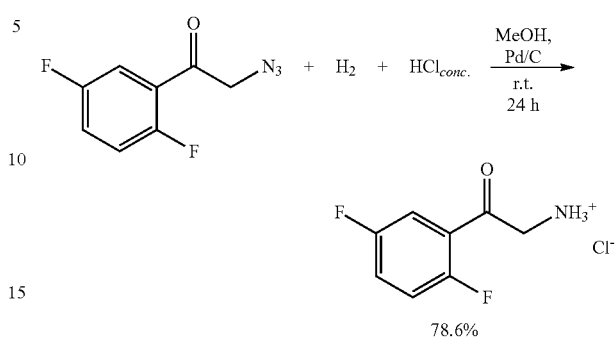

A methanolic solution (200 mL) of 2-azido-1-(2,5-difluorophenyl)ethanone (13.39 g, 67.92 mmol) containing 5% Pd/C (1.34 g), conc. HCl (8.6 mL) is left stirring under hydrogen at room temperature (rt) for 24 h. The resulting reaction mixture is filtered through Celite and concentrated at the rotoevaporator. The resulting solid is suspended in AcOEt (50 mL), filtered and washed with AcOEt (50 mL) to obtain 11.09 g of a colourless product (79% yield).

Example 3

Synthesis of the Compound of Formula (I) in Which P is Boc and R$^1$ is Propargyl, i.e. tert-butyl 1-(2,5-difluorophenyl)-1-oxopent-4-yn-2-ylcarbamate, Using Propargyl Bromide

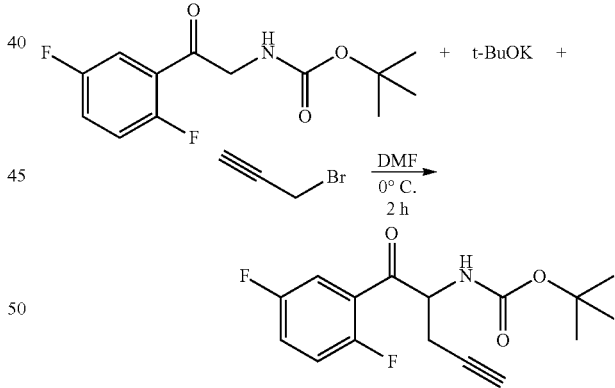

To an ice cooled solution of t-butyl 2-(2,5-difluorophenyl)-2-oxoethyl carbamate (100 mg, 0.360 mmol) in anhydrous DMF (1.5 mL) (DMF=dimethylformamide), t-BuOK (49 mg, 0.432 mmol) is added under Ar. Propargyl bromide (43 mg, 0.36 mmol) is added to the resulting red coloured solution while stirring. The reaction mixture is left reaching room temperature within 2 h, water (100 mL) is added and the mixture is extracted with Et$_2$O (3×20 mL). The combined organic layers are washed with brine (3×20 mL), dried (MgSO$_4$) and evaporated under reduced pressure to give 100 mg (90% yield) of tert-butyl 1-(2,5-difluorophenyl)-1-oxopent-4-yn-2-yl carbamate.

Example 4

Synthesis of the Compound of Formula (I) in Which P is Boc (t-buthyloxycarbonyl) or Cbz (Benzyloxycarbonyl) and R¹ is Propargyl or Allyl Comprehensive Scheme of Synthesis:

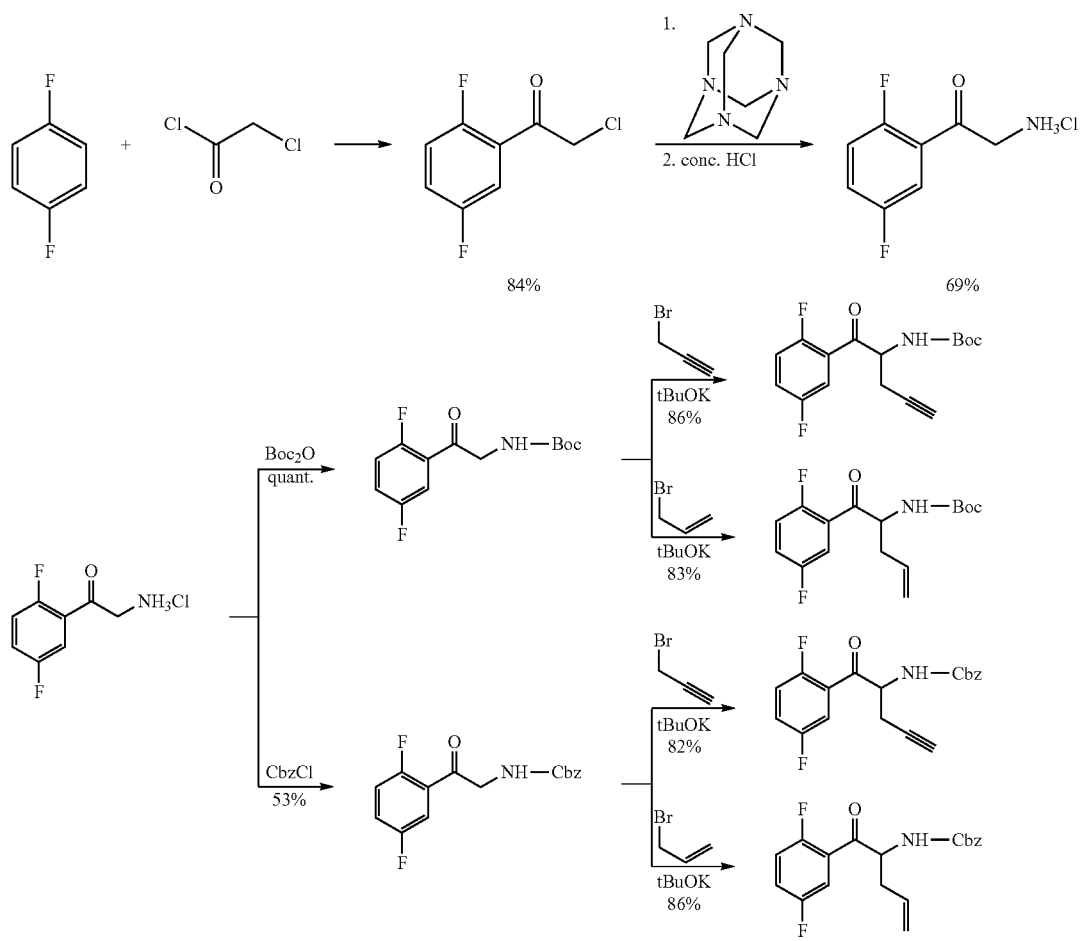

STEP (a)-part I: Synthesis of 1-(2,5-difluorophenyl)ethanone-2-hexamethylentetrammonium chloride

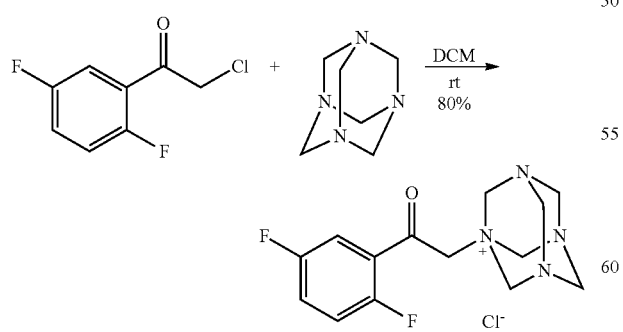

A solution of 2-chloro-1-(2,5-difluorophenyl)ethanone (5 g, 26.2 mmol), Hexamine (also named Hexamethylenetetramine or HMTA) (4.05 g, 28.9 mmol) in 50 mL of dichloromethane is left under stirring at room temperature for 18 hour and then the solvent was removed by concentration to dryness with the rotavapor. The residual solid was taken up with acetone and the suspension was filtered washing the solid with acetone. 6.97 of 1-(2,5-difluorophenyl)ethanone-2-hexamethylentetrammonium chloride as white solid were collected. Molar yield 80%.

STEP (a)-Part II: Synthesis of 2-(2,5-difluorophenyl)-2-oxoethanammonium chloride or 2-(2,5-difluorophenyl)-2-oxoethanammine hydrochloride

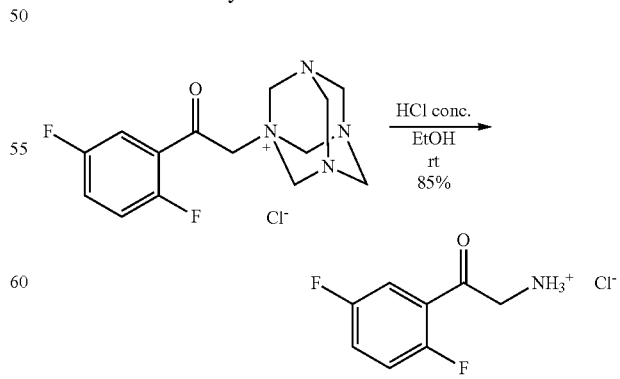

A solution of 1-(2,5-difluorophenyl)ethanone-2-hexamethylentetrammonium chloride (3.5 g, 10.6 mmol) in ethanol (60 mL) and conc. HCl 37% (7.5 mL) and is left under stirring for 72 hours, then the solution was concentrated to dryness with the rotavapor. The mixture was taken up with hot isopropanol and was hot filtered. The filtrated was concentrated to dryness and the solid residual was washed with 20 ml of dichloromethane and 20 ml of acetone. 1.51 g of slightly yellow solid were obtained. Molar yield of 85%.

STEP (b): Synthesis of the Compound of Formula (II) Wherein P is Cbz, i.e. Synthesis of benzyl 2-(2,5-difluorophenyl)-2-oxoethylcarbamate

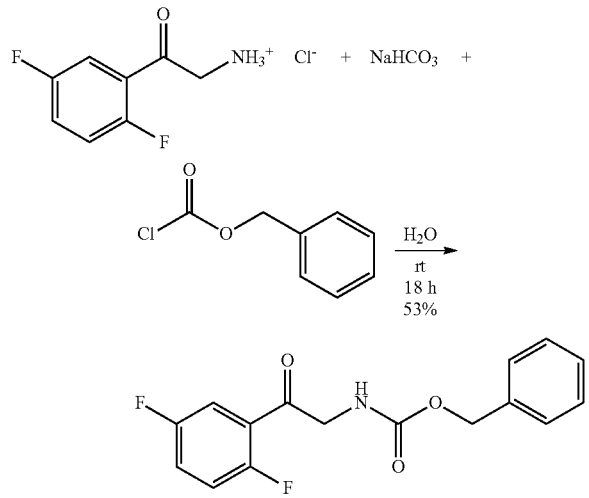

To a solution of 2-(2,5-difluorophenyl)-2-oxoethanammonium chloride (0.63 g, 3.03 mmol) and NaHCO$_3$ (0.64 g, 7.59 mmol) in H$_2$O (30 mL) kept under Argon atmosphere, benzyl chloroformate (0.65 mL, 4.55 mmol) was slowly added, and the mixture was stirred for 18 hours at room temperature. The mixture was extracted with Et$_2$O (3×50 mL). The organic phases were re-joined and then washed with brine (50 mL), anhydrified on MgSO$_4$ anhydrous and concentrated with the rotavapor. The crude product thus obtained was further purified by means of chromatography on silica (eluent cyclohexane/ether with gradient from 9:1 to 6:4) thus obtaining the product benzyl 2-(2,5-difluorophenyl)-2-oxoethylcarbamate as a white solid (0.49 g, 53% molar yield). $^1$H-NMR (200 MHz, CDCl$_3$): δ=7.61-7.70 (m, 1 H), 7.11-7.40 (m, 7 H), 5.69 (s, br, 1 H), 5.15 (s, 2 H), 4.65 (t, J=4.0 Hz, 2 H) ppm.

STEP (c): Synthesis of the Compound of Formula (I) Wherein R$^1$ is Propargyl and P is Cbz, i.e. Synthesis of benzyl 1-(2,5-difluorophenyl)-1-oxopent-4-yn-2-ylcarbamate

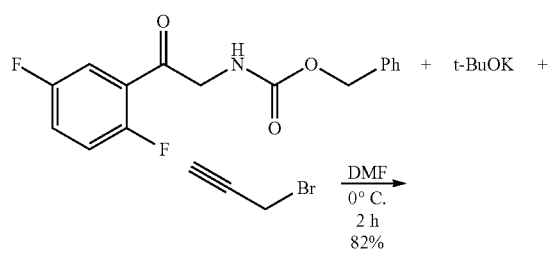

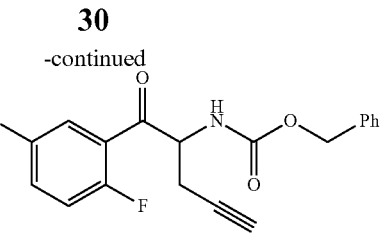

To a solution of benzyl 2-(2,5-difluorophenyl)-2-oxoethylcarbamate (122 mg, 0.40 mmol) in anhydrous dimethylfomamide (DMF) (2 mL) kept under Argon atmosphere at 0° C., t-BuOK (54 mg, 0.48 mmol) was added and the mixture was left under stirring for 20 minutes. To the resulting red solution, at 0° C., propargyl bromide (at 80% in solution of toluene, 54 µL, 0.48 mmol) was added and the mixture was left under stirring for 2 hours. Et$_2$O (5 mL) was then added, and the suspension was filtered on celite and the filtrate was concentrated under vacuum. The crude product thus prepared was further purified by means of chromatography on silica (eluent cyclohexane/ether in gradient from 10:0 to 8:2) obtaining the product as a white solid (112 mg, 82% molar yield). $^1$H-NMR (300 MHz, CDCl$_3$): δ=7.54-7.59 (m, 1 H), 7.22-7.37 (m, 6 H), 7.11-7.18 (m, 1 H), 6.00 (d, J=7.9 Hz, 1 H), 5.28-5.35 (m, 1 H), 5.13 (s, 2 H), 2.96 (dm, J=17.4 Hz, 1 H), 2.70 (dm, J=17.4 Hz, 1H), 1.99 (t, J=2.6 Hz, 1H) ppm.

STEP (c): Synthesis of the Compound of Formula (I) Wherein R$^1$ is Allyl and P is Cbz, i.e. Synthesis of benzyl 1-(2,5-difluorophenyl)-1-oxopent-4-en-2-ylcarbamate

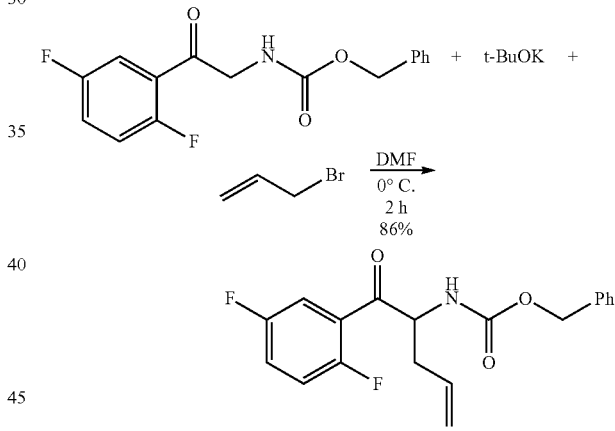

To a solution of benzyl 2-(2,5-difluorophenyl)-2-oxoethylcarbamate (122 mg, 0.40 mmol) in anhydrous DMF (2 mL) kept under Argon atmosphere at 0° C., t-BuOK (54 mg, 0.48 mmol) was added and the mixture was left under stirring for 20 minutes. To the resulting red solution, at 0° C., allyl bromide (42 µL, 0.48 mmol) was added and the mixture was left under stirring for 2 hours. Et$_2$O (5 mL) was then added and the mixture was filtered on celite and concentrated under vacuum. The crude product thus obtained was further purified by means of chromatography on silica (eluent cyclohexane/ether with gradient from 10:0 to 8:2) obtaining the product as white solid (119 mg, 86% molar yield). $^1$H-NMR (300 MHz, CDCl$_3$): δ=7.53-7.59 (m, 1 H), 7.22-7.37 (m, 6 H), 7.11-7.19 (m, 1 H), 5.58-5.72 (m, 2 H), 5.26-5.32 (m, 1 H), 5.12 (s, 2 H), 4.99-5.10 (m, 2 H), 2.69-2.78 (m, 1 H), 2.33-2.42 (m, 1 H) ppm.

STEP (c): Synthesis of the Compound of Formula (I) Wherein R$^1$ is Propargyl and P is Boc, i.e. Synthesis of tert-butyl 1-(2,5-difluorophenyl)-1-oxopent-4-yn-2-ylcarbamate

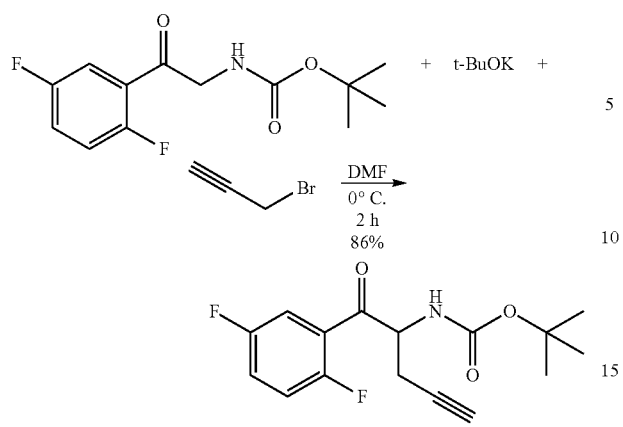

To a solution of tert-butyl 2-(2,5-difluorophenyl)-2-oxo-ethylcarbamate (136 mg, 0.50 mmol) (as prepared in Example 1 Step (b)) in anhydrous DMF (2 mL) kept under Argon atmosphere at 0° C., t-BuOK (67.3 mg, 0.60 mmol) was added and the mixture was left under stirring for 20 minutes. To the resulting red solution, at 0° C., propargyl bromide (80% in toluene solution, 67 μL, 0.60 mmol) was added and the mixture was left under stirring for 2 h. Et$_2$O (5 mL) was then added and the suspension was filtered on celite and concentrated under vacuum. The crude product thus obtained was further purified by means of chromatography on silica (eluent cyclohexane/ether with gradient from 10:0 to 8:2) obtaining the product as white solid (133 mg, 86% molar yield). $^1$H-NMR (300 MHz, CDCl$_3$): δ=7.50-7.56 (m, 1 H), 7.20-7.28 (m, 1 H), 7.09-7.16 (m, 1 H), 5.68 (d, J=7.7 Hz, 1 H), 5.22-5.27 (m, 1 H), 2.88 (dm, J=17.3 Hz, 1 H), 2.65 (dm, J=17.3 Hz, 1 H), 1.98 (t, J=2.6 Hz, 1 H), 1.42 (s, 9 H) ppm.

Step (c): Synthesis of the Compound of Formula (I) Wherein R$^1$ is Allyl and P is Boc, i.e. Synthesis of tert-butyl 1-(2,5-difluorophenyl)-1-oxopent-4-en-2-ylcarbamate

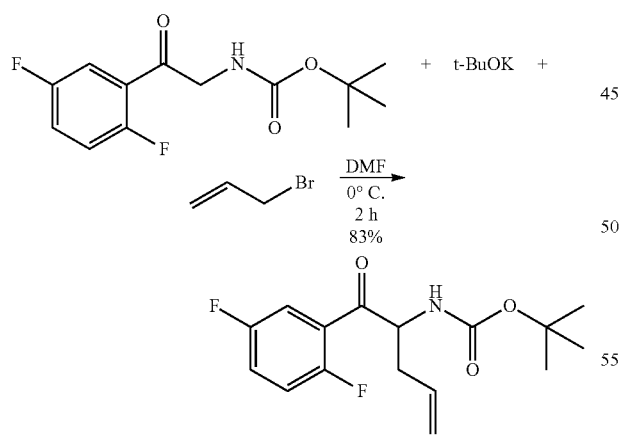

To a solution of tert-butyl 2-(2,5-difluorophenyl)-2-oxo-ethylcarbamate (136 mg, 0.50 mmol) (as prepared in Example 1 Step (b)) in anhydrous DMF (2 mL) kept under Argon atmosphere at 0° C., t-BuOK (67.3 mg, 0.60 mmol) was added and the mixture was left under stirring for 20 minutes. To the resulting red solution, at 0° C., allyl bromide (52 μL, 0.60 mmol) was added and the mixture was left under stirring for 2 hours. Et$_2$O (5 mL) was added and the mixture was filtered on celite and concentrated under vacuum. The crude product thus obtained was further purified by means of chromatography on silica (eluent cyclohexane/ether in gradient from 10:0 to 8:2) obtaining the product as colorless oil (129 mg, 83% molar yield). $^1$H-NMR (300 MHz, CDCl$_3$): δ=7.52-7.57 (m, 1 H), 7.21-7.28 (m, 1 H), 7.10-7.18 (m, 1 H), 5.59-5.73 (m, 1 H), 5.37 (d, J=8.1 Hz, 1 H), 5.17-5.23 (m, 1 H), 5.00-5.10 (m, 2 H), 2.65-2.74 (m, 1 H), 2.26-2.39 (m, 1 H), 1.43 (s, 9 H) ppm.

The invention claimed is:

1. Process for the preparation of the compound of formula (I):

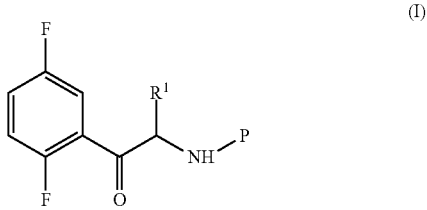

wherein R$^1$ is propargyl or allyl group and P is an amine protecting group comprising:
(a) converting the compound of formula (IV):

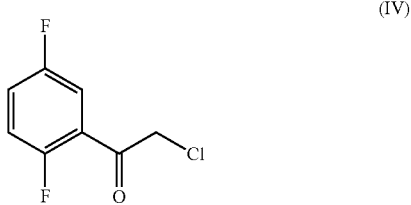 [SMILES: O=C(CCl)c1cc(F)ccc1F]

by an amination reaction to provide the compound of formula (III) or salt thereof:

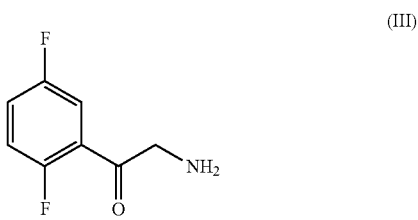 [SMILES: NCC(=O)c1cc(F)ccc1F]

(b) protecting the compound of formula (III) to provide the compound of formula (II):

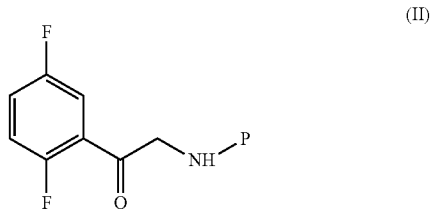

wherein P is an amine protecting group and
(c) alkylating the compound of formula (II) to provide the compound of formula (I):

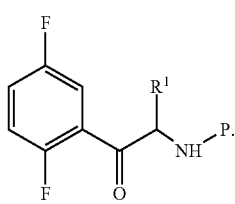
(I)

2. Process according to the claim 1, wherein step (a) is carried out by amination reaction with hexamethylenetramine.

3. Process according to the claim 1, wherein step (a) is carried out through the following steps:

(a1) converting the compound of formula (IV):

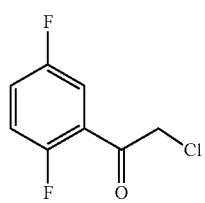
(IV)

by an azidation reaction to provide the compound of formula (V):

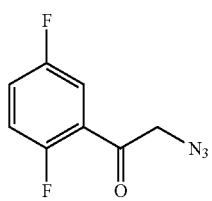
(V)

and (a2) reducing the compound of formula (V) to provide the compound of formula (III) or salt thereof:

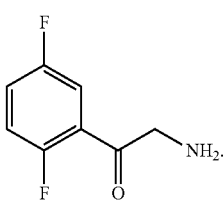
(III)

4. Process according to claim 1 wherein $R^1$ is propargyl.

5. Process according to claim 1 wherein P is t-butyloxycarbonyl.

6. Process according to claim 1 wherein $R^1$ is propargyl and P is t-butyloxycarbonyl.

7. A compound selected from the group consisting of:
the compound of formula (III) as hydrochloride or hydrobromide salt:

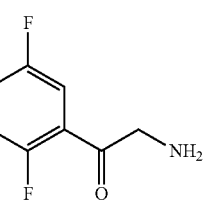
(III)

and
the compound of formula (II):

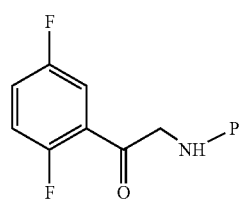
(II)

wherein P is an amine protecting group that is formyl, acetyl, benzoyl, phenylsulfonyl, tolylsulfonyl, methylsulfonyl, $(CO)OR^2$ or $(CO)R^2$ where $R^2$ is an optionally substituted $C_{1-5}$ linear or branched alkyl or $R^2$ is aryl-$C_{0-4}$ alkyl or $C_{0-4}$ alkyl-(unsubstituted or substituted aryl).

8. Compound according to claim 7 wherein P is t-butyloxycarbonyl or benzyloxycarbonyl.

9. Compound of formula (I):

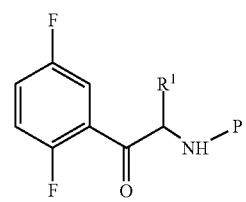
(I)

wherein $R^1$ is allyl group and P is a amine protecting group.

10. Compound according to claim 9, selected from the group consisting of:
benzyl 1-(2,5-difluorophenyl)-1-oxopent-4-en-2-ylcarbamate, and
tert-butyl 1-(2,5-difluorophenyl)-1-oxopent-4-en-2-ylcarbamate.

11. Process for the preparation of the compound of formula (X):

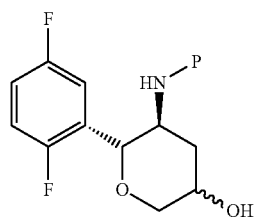
(X)

wherein P is an amine protecting group, comprising:

a) preparing the compound of formula (I):

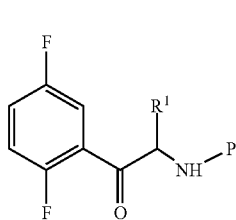

(I)

wherein R¹ is propargyl or allyl group and P is an amine protecting group, according to the process of claim 1, and b) converting the compound of formula (I) prepared in step a) to compound of formula (X) by (d) converting the compound of formula (I):

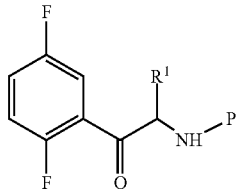

(I)

wherein R¹ is propargyl group and P is an amine protecting group, to the compound of formula (VI):

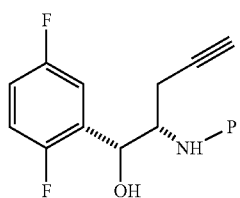

(VI)

wherein P is an amine protecting group;

(e) converting the compound of formula (VI) with a ruthenium catalyst:

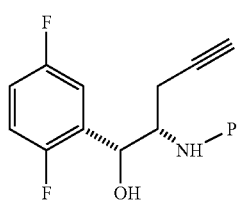

(VI)

wherein P is an amine protecting group, to the compound of formula (VII):

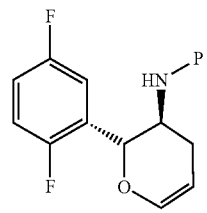

(VII)

wherein P is an amine protecting group, (f) converting the compound of formula (VII) with $NaBO_3$ or $BH_3$—$SMe_2$:

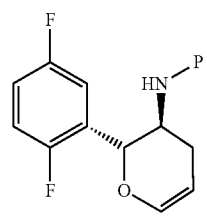

(VII)

wherein P is an amine protecting group, to the compound of formula (X):

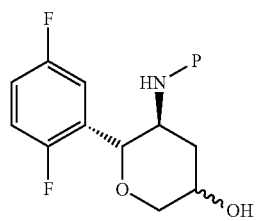

(X)

wherein P is an amine protecting group, or, alternatively, process wherein the steps (d), (e), (f) are substituted by the following steps (j), (k), (l):

(j) converting the compound of formula (I):

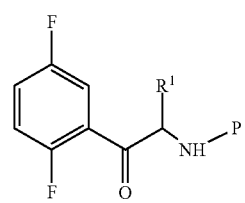

(I)

wherein R¹ is allyl group and P is an amine protecting group, to the compound of formula (VIII):

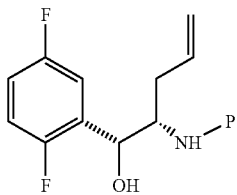
(VIII)

wherein P is an amine protecting group;

(k) converting the compound of formula (VIII):

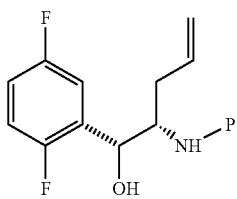
(VIII)

wherein P is an amine protecting group,
to the compound of formula (IX):

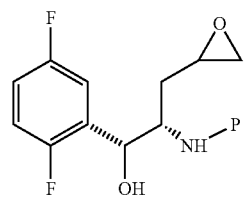
(IX)

wherein P is an amine protecting group, (l) converting the compound of formula (IX) by a 6-endo-type cyclization of epoxide reaction:

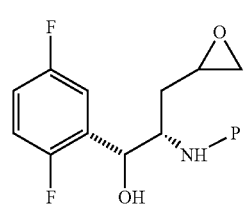
(IX)

wherein P is an amine protecting group, to the compound of formula (X):

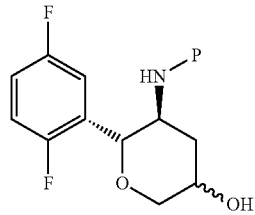
(X)

wherein P is an amine protecting group.

12. Process for the preparation of the Omarigliptin of formula (XIV):

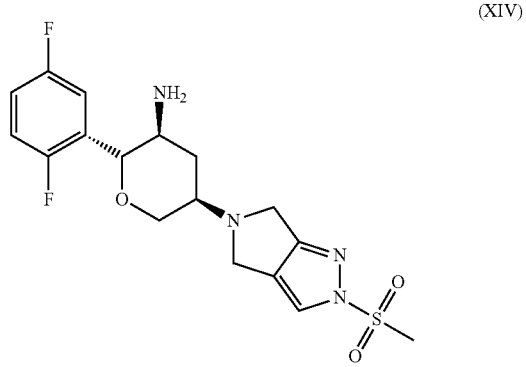
(XIV)

comprising preparing the compound of formula (X):

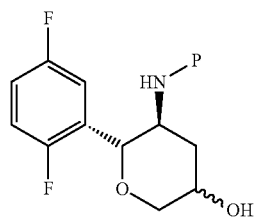
(X)

wherein P is an amine protecting group, according to the process of claim 11, and the following further steps:

(g) converting the compound of formula (X):

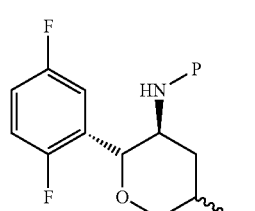
(X)

wherein P is an amine protecting group, to the compound of formula (XI):

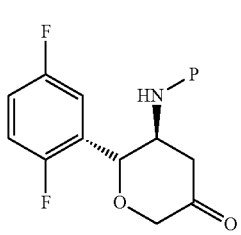
(XI)

wherein P is an amine protecting group,
(h) reacting of the compound of formula (XI):

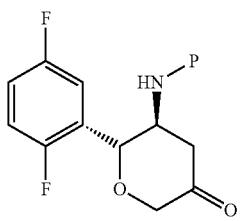
(XI)

wherein P is an amine protecting group,
with the compound of formula (XII) or salt thereof:

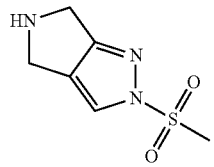
(XII)

to provide the compound of formula (XIII):

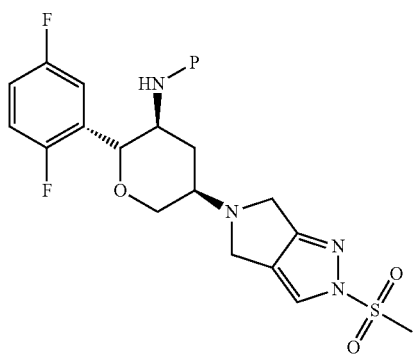
(XIII)

wherein P is an amine protecting group, (i) converting the compound of formula (XIII):

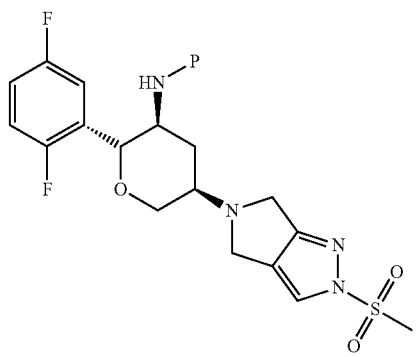
(XIII)

wherein P is an amine protecting group,
to Omarigliptin of formula (XIV):

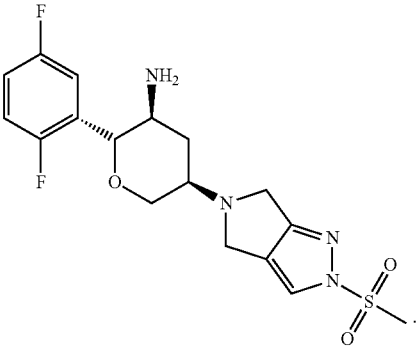
(XIV)

13. Process according to claim 11 wherein in the compounds of formula (I), (VI), (VII), (VIII), (IX), or (X), the amine protecting group P is t-butyloxycarbonyl.

14. The compound of claim 7, wherein the linear or branched $C_{1-5}$ alkyl group of $R^2$ is unsubstituted or substituted with one, two or three substituents chosen from the group consisting of hydroxyl and $C_{1-5}$ alkoxy.

15. The compound of claim 7, wherein the linear or branched $C_{1-5}$ alkyl group of $R^2$ is methyl, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, or 1-ethylpropyl.

16. Process according to claim 12 wherein in the compound of formula (XI), the amine protecting group P is t-butyloxycarbonyl.

17. Process according to claim 12 wherein in the compound of formula (XIII), the amine protecting group P is t-butyloxycarbonyl.

* * * * *